US007060027B2

(12) United States Patent
Maeda et al.

(10) Patent No.: US 7,060,027 B2
(45) Date of Patent: Jun. 13, 2006

(54) ELECTRIC BENDING ENDOSCOPE APPARATUS

(75) Inventors: Toshinari Maeda, Hachioji (JP);
Keiichi Arai, Hachioji (JP); Takemitsu Honda, Hino (JP); Seiichiro Kimoto, Hachioji (JP); Takayasu Miyagi, Hachioji (JP); Yuichi Ikeda, Tama (JP); Toshimasa Kawai, Yokohama (JP)

(73) Assignee: Olympus Corporation, Tokyo (JP)

( * ) Notice: Subject to any disclaimer, the term of this patent is extended or adjusted under 35 U.S.C. 154(b) by 93 days.

(21) Appl. No.: 10/395,780

(22) Filed: Mar. 24, 2003

(65) Prior Publication Data
US 2004/0054258 A1    Mar. 18, 2004

(51) Int. Cl.
*A61B 1/00* (2006.01)
(52) U.S. Cl. ............ 600/150; 600/117; 600/118; 600/145; 600/146
(58) Field of Classification Search ............ 600/103, 600/149, 117–118, 145–146, 150
See application file for complete search history.

(56) References Cited

U.S. PATENT DOCUMENTS

| | | | | |
|---|---|---|---|---|
| 5,159,446 | A * | 10/1992 | Hibino et al. | 348/65 |
| 5,469,840 | A * | 11/1995 | Tanii et al. | 600/117 |
| 5,658,238 | A * | 8/1997 | Suzuki et al. | 600/150 |
| 5,733,245 | A * | 3/1998 | Kawano | 600/144 |
| 5,788,694 | A * | 8/1998 | Vancaillie | 606/45 |
| 6,174,280 | B1 * | 1/2001 | Oneda et al. | 600/121 |
| 6,315,714 | B1 * | 11/2001 | Akiba | 600/114 |
| 6,638,213 | B1 * | 10/2003 | Ogura et al. | 600/148 |
| 2002/0161281 | A1 * | 10/2002 | Jaffe et al. | 600/114 |
| 2002/0165430 | A1 * | 11/2002 | Matsui | 600/118 |
| 2003/0195389 | A1 * | 10/2003 | Motoki et al. | 600/146 |
| 2004/0034279 | A1 * | 2/2004 | Arai et al. | 600/152 |
| 2004/0124717 | A1 * | 7/2004 | Corcoran et al. | 310/12 |
| 2004/0193016 | A1 * | 9/2004 | Root et al. | 600/146 |

FOREIGN PATENT DOCUMENTS

JP    6-269398    9/1994

* cited by examiner

*Primary Examiner*—John Leubecker
*Assistant Examiner*—Philip R Smith
(74) *Attorney, Agent, or Firm*—Scully, Scott, Murphy & Presser, P.C.

(57) ABSTRACT

Driving force of a bending motor is transmitted to a sprocket via a clutch mechanism portion. The operation of a switching operation lever switches the clutch mechanism portion to a disconnecting/restoring status. A bending control device includes a bending angle calculating portion which calculates information on a bending status based on an output signal of a potentiometer, a motor driving signal generating portion which generates a driving signal for bending a bending portion, a JS-motor driving signal generating portion which calculates a position for an instructing status of a stick portion based on the information on the bending status and generates the driving signal for moving the stick portion to the position, and a calibration instructing portion which receives a position signal from a status detecting switch and which sends an instruction for outputting to a JS motor, the driving signal generated by the JS-motor driving signal generating portion. With the above construction, the calibration operation is easily performed in a freely bending status.

16 Claims, 11 Drawing Sheets

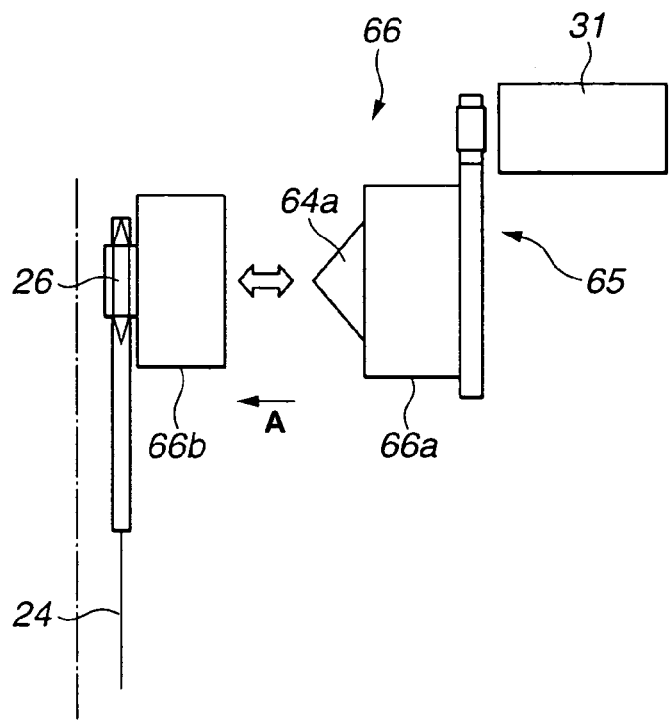
FIG.11A
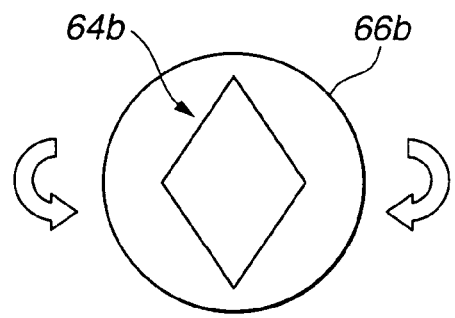
FIG.11B
FIG.14
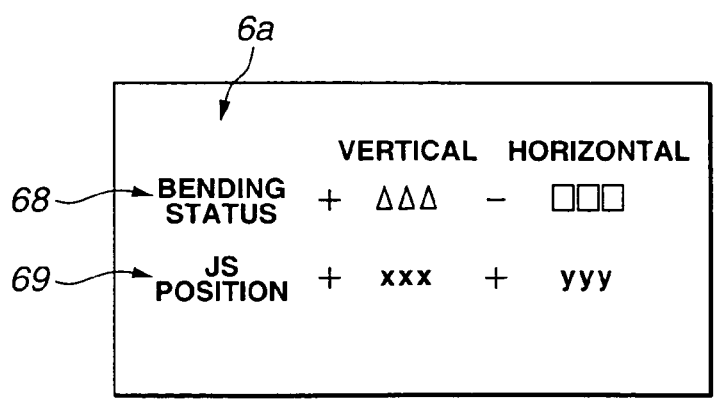

ELECTRIC BENDING ENDOSCOPE APPARATUS

BACKGROUND OF THE INVENTION

1. Field of the Invention

The present invention relates to an electric bending endoscope apparatus having an electric bending endoscope which electrically bends a bending portion in a status corresponding to an absolute-position signal by operating bending operation instructing means for outputting the absolute-position signal.

2. Description of the Related Art

Recently, an endoscope is widely used for various curing treatments which are performed by inserting an elongated inserting portion in the celom so as to observe the organ in the celom or by using a treatment tool inserted in a treatment tool channel as needed.

The endoscope generally has a bending portion which is bent vertically or horizontally on a distal portion side. The bending portion is bent in a desired direction by stretching and contracting a bending wire connected to the bending portion.

In general, the bending wire is manually operated. However, the endoscope recently includes an electric bending endoscope which is stretched by bending motive means such as an electric motor. In the electric bending endoscope, the electric motor is rotated by a joystick for outputting a bending instructing signal of an absolute position, such as bending operation instructing means arranged to an operating portion. Then, the rotation of the electric motor rotates a pulley, the bending wire connected to the pulley is stretched, and the bending portion is bent.

The joystick instructs a bending position by being inclined. That is, a direction for inclining the joystick is one for bending the bending portion and an inclining angle of the joystick corresponds to a bending angle of the bending portion. When the inclining angle of the joystick is 0° as a straight status, the bending portion is in a non-bending status (straight status). Therefore, an operator can easily grasp a bending status of the bending portion in the celom with his sense of the finger which grips the joystick.

Namely, in the above-mentioned electric bending endoscope, the bending portion is easily and desirably bent by the single finger. Accordingly, the operability is improved because another finger operates other switches arranged to the operating portion. However, in the electric bending endoscope, the bending wire is always under tension irrespective of in the bending status or non-bending status. Then, the following is requested to the electric bending endoscope.

(1) Since the bending wire has a tendency to stretch by the tension, the stretch of the bending wire is prevented.

(2) The bending wire is not under the tension during manual inserting operation, and the bending portion is in a freely bending status by external force.

(3) When a default is caused during the inserting operation, the inserting portion is removed in the freely bending status.

Endoscopes to respond to the above requests are proposed. For example, an electric bending endoscope has means for restoring transmission and disconnection of driving force which can switch a status for disconnecting the transmission of driving force/a status for restoring the transmission of the driving force of the tension acting on the bending wire in accordance with the necessity. Further, Japanese Unexamined Patent Application Publication No. 6-269398 discloses an endoscope which surely switches a locking status and a free status of the bending portion by arranging status switching means which can switch a stretching status and a contracting status of a stretching member.

SUMMARY OF THE INVENTION

According to the present invention, an electric bending endoscope apparatus comprises: an electric bending endoscope having a bending portion at an inserting portion thereof and a bending driving portion with a plurality of members for bending the bending portion; a bending motive device which drives the bending driving portion; a bending angle detecting portion which detects an operating status of the bending driving portion and detects a bending status of the bending portion; a bending operation instructing portion having an instructing member which outputs a bending instructing signal for bending the bending portion, matching an instructing status of the instructing member to the bending status of the bending portion with a positional relationship; a bending control device comprising a driving signal generating portion which generates a driving signal outputted to the bending motive device based on the bending instructing signal outputted from the bending operation instructing portion and information on a bending position indicating the bending status detected by the bending angle detecting portion; a portion for restoring transmission and disconnection of driving force which reversibly switches a transmitting status for transmitting the driving force of the bending motive device to the bending driving portion or a disconnecting status; and a positioning portion which relatively matches the instructing status of the instructing member in the bending operation instructing portion to the bending status of the bending portion.

The above and other objects, features and advantages of the invention will become more clearly understood from the following description referring to the accompanying drawings.

BRIEF DESCRIPTION OF THE DRAWINGS

FIGS. 11A and 11B are diagrams for explaining the construction of a clutch mechanism portion for the calibration operation;

FIG. 14 is a diagram for explaining an image which is superimposed and displayed on a screen of a monitor.

DESCRIPTION OF THE PREFERRED EMBODIMENTS

Hereinbelow, embodiments of the present invention will be described with reference to the drawings.

Figure 1:
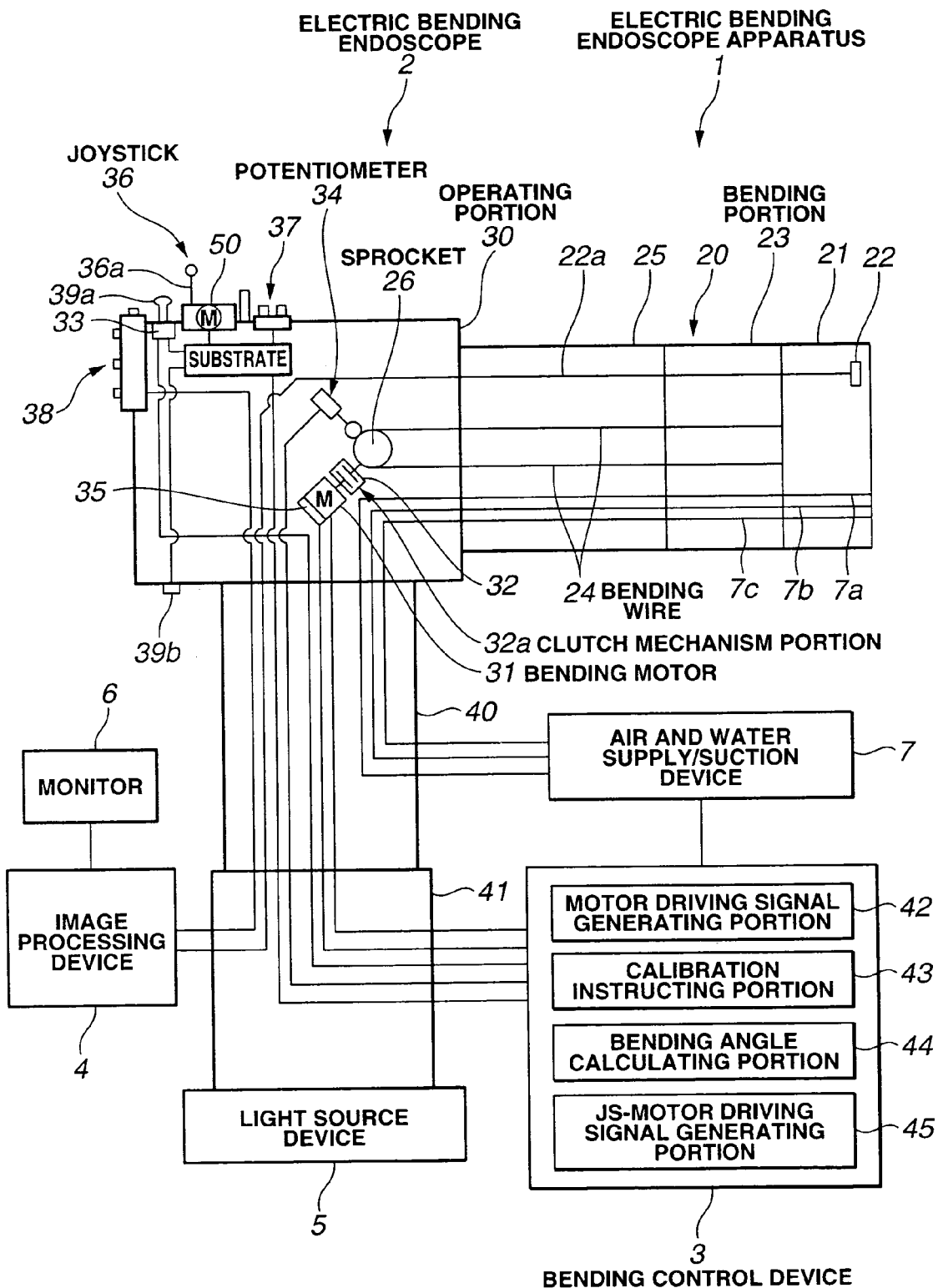
FIG. 1 is a diagram showing the construction of an electric bending endoscope apparatus according to a first embodiment.
Figure 2:
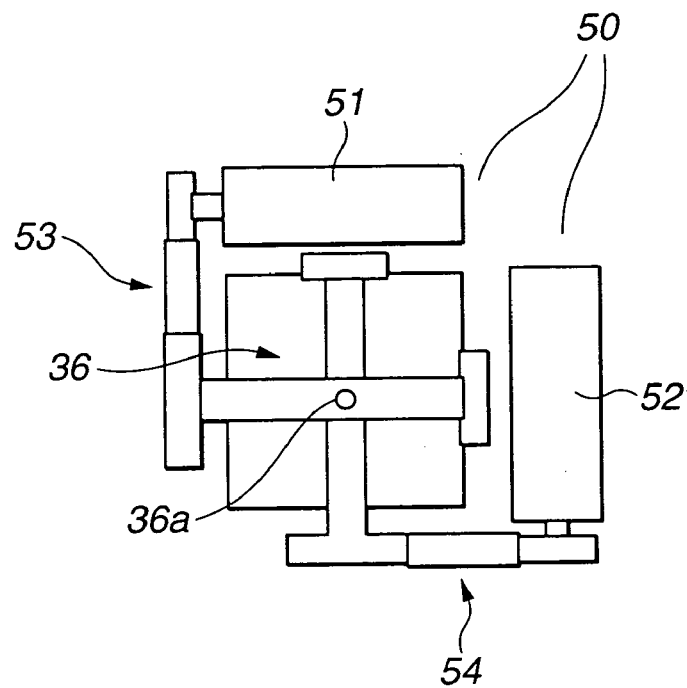
FIG. 2 is a diagram for explaining a joystick having a motor for a stick portion.
Figure 4:
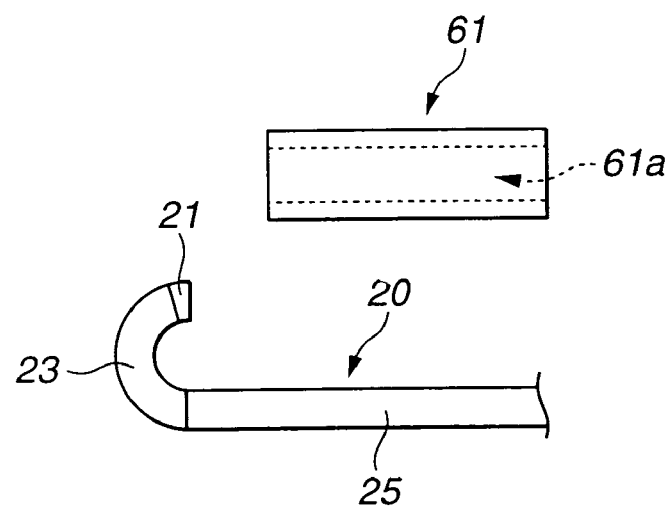
FIG. 4 is a diagram for explaining a non-bending status setting tool.
Figure 3:
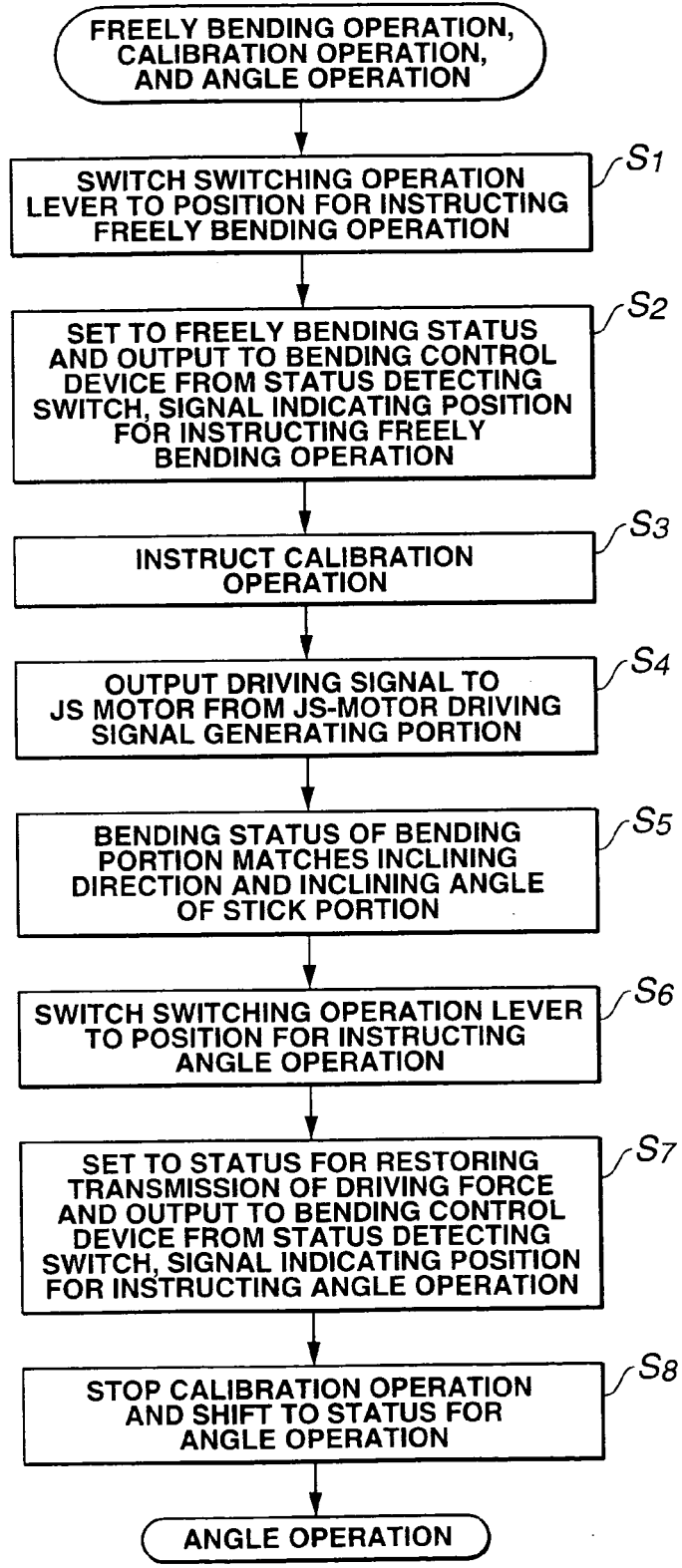
FIG. 3 is a flowchart for explaining a freely bending operation, a calibration operation, and an angle operation.
Figure 5:
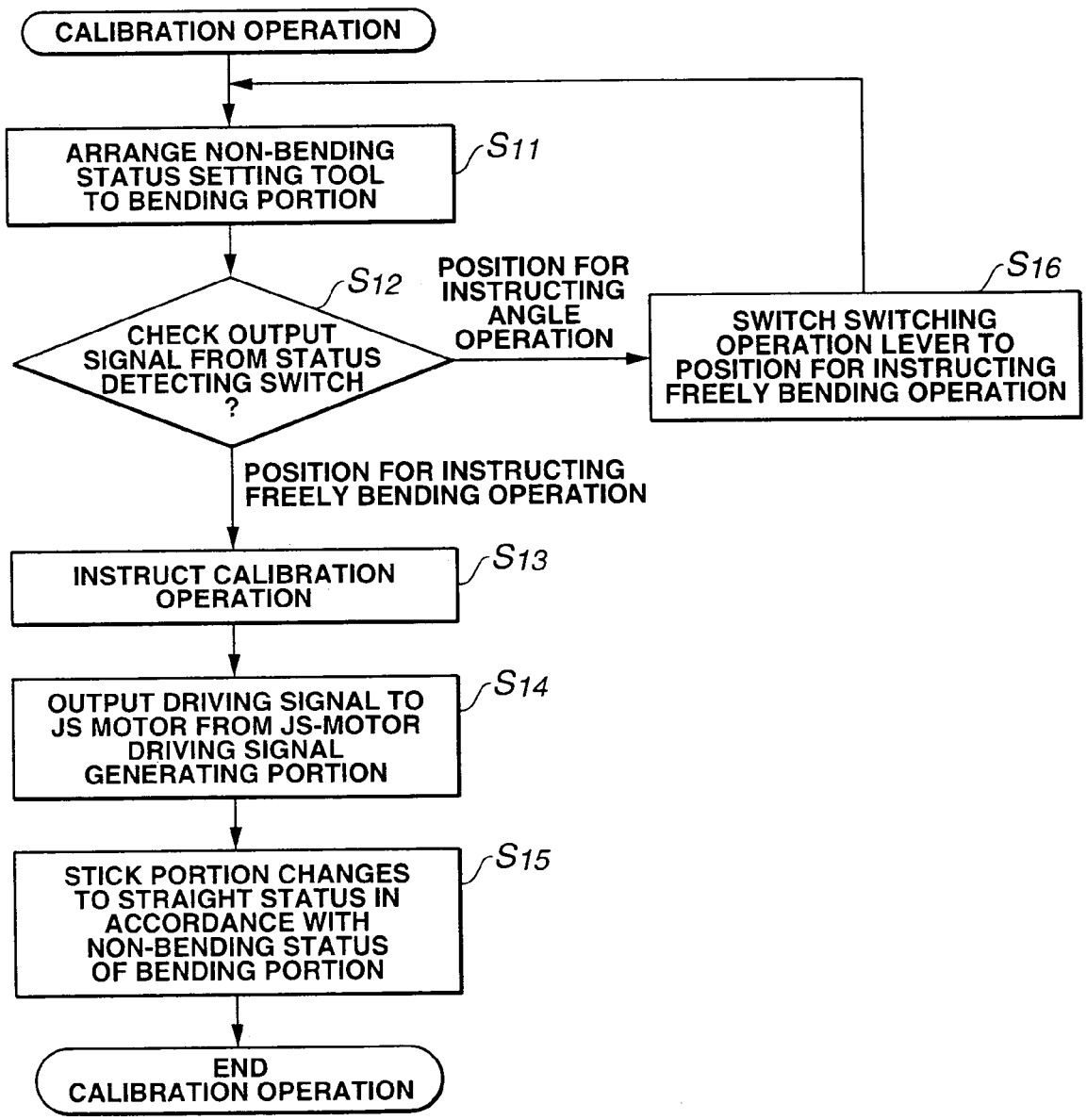
FIG. 5 is a flowchart for explaining the calibration operation.

A first embodiment of the present invention will be described with reference to FIGS. 1 to 5. FIG. 1 is a diagram showing the construction of an electric bending endoscope apparatus. FIG. 2 is a diagram for explaining a joystick having a motor for a stick portion. FIG. 3 is a flowchart for explaining a freely bending operation, a calibration operation, and an angle operation. FIG. 4 is a diagram for explaining a non-bending status setting tool. FIG. 5 is a flowchart for explaining the calibration operation.

Referring to FIG. 1, an electric bending endoscope apparatus 1 according to the first embodiment comprises an electric bending endoscope (hereinafter, referred to as an endoscope) 2, a bending control device 3, an image processing device 4, a light source device 5 which supplies illumination light to an illumination optical system (not shown) via a light guide fibers (not shown), and a monitor 6 as a display device which displays an endoscope image by outputting the video signal generated by the image processing device 4.

The endoscope 2 has a distal forming portion 21 forming an endoscope inserting portion (hereinafter, referred to as an inserting portion) 20. The distal forming portion 21 incorporates an image pick-up device 22. A bending portion 23 is arranged on a proximal side of the distal forming portion 21. The bending portion 23 is bent by electrically stretching bending wires 24 forming bending driving means. The bending wires 24 are stretched by a bending motor which will be described later. The driving operation of the bending motor is controlled by a motor driving signal generated by a motor driving signal generating portion 42 in the bending control device 3. The image processing device 4 transmits an image signal via a signal cable 22a extending from the image pick-up device 22, subjects predetermined signal processing to the image signal, and generates a video signal.

The inserting portion 20 includes, e.g., an air channel 7a, a water channel 7b, and a suction line 7c. The air channel 7a, the water channel 7b, and the suction line 7c are connected to an air and water supply/suction device 7. The bending control device 3 and the image processing device 4 are electrically connected via a signal line (not shown).

The endoscope 2 comprises the elongated inserting portion 20, an operating portion 30 commonly functioning as a grip portion, and a universal cord 40 extending from a side portion of the operating portion 30. A connector portion 41 connected to the light source device 5 is arranged at the base end portion of the universal cord 40.

The inserting portion 20 comprises the distal forming portion 21 incorporating the image pick-up device 22 such as a CCD, an observation optical system, the bending portion 23 which is connected to the distal forming portion 21, and an elongated and soft flexible-line portion 25 which is connected to the bending portion 23. The bending portion 23 has a plurality of bending pieces continuously arranged (not shown) and are formed to freely be bent vertically and horizontally.

The inserting portion 20 includes the vertical bending wires 24 and horizontal bending wires (not shown), which bend the bending portion 23, extending from the operating portion 30.

Hereinbelow, a description is given of the structure of the vertical bending wires 24. Further, the structure of the horizontal bending wires with the same structure as that of the vertical bending wires 24 is neither shown nor mentioned for the sake of a brief description.

Both end portions of the bending wire 24 are connected and fixed to a chain (not shown). The chain meshes with a rotatable vertical sprocket 26 forming the bending driving means. Thus, the bending wire 24 fixed to the chain is stretched by rotating the sprocket 26 in a predetermined direction. Then, the bending portion 23 is bent in a predetermined direction.

The sprocket 26 is arranged in the operating portion 30. In the sprocket 26, driving force of the vertical bending motor 31 comprising a DC motor as bending motive means is transmitted via a transmitting portion with a clutch mechanism (hereinafter, referred to as a transmitting portion with a clutch) 32 having a plurality of trains of gears (not shown) and a clutch mechanism portion 32a which detaches engaged gears as means for restoring transmission and disconnection of the driving force. The transmitting portion 32 with the clutch prevents the tension to the bending wire 24 and, thus, the bending portion 23 enters a freely bending status in which it is freely bent by external force.

The transmitting portion 32 with the clutch can switch a status for disconnecting the transmission of the driving force as a disconnecting status of the clutch mechanism portion 32a and a status for restoring the transmission of the driving force as a connecting status of the clutch mechanism portion 32a by switching a switching lever 39a as status switching means to a position for disconnecting the transmission of the driving force (hereinafter, referred to as a position for instructing the freely bending operation) and to a position for restoring the transmission of the driving force (hereinafter, referred to as a position for instructing an angle operation).

That is, the clutch mechanism portion 32a in the transmitting portion 32 with the clutch is mechanically switched to the disconnecting status or the connecting status by switching the switching operation lever 39a. Consequently, the bending motor 31 and the sprocket 26 are reversibly detached.

The amount of rotation of the sprocket 26 is detected by a potentiometer 34 as means for detecting a bending angle. Reference numeral 35 denotes an encoder which detects the amount of rotation of the bending motor 31.

The operating portion 30 comprises a joystick 36 having a motor 50 for a stick portion as means for instructing the bending operation that bends the bending portion 23, which outputs a position signal of information on an absolute position as a signal for instructing the bending operation, as will be described later, an air and water supply/suction switch 37 which instructs an air supply status, a water supply status, or a suction status, various scope switches 38 which control the image processing device 4 such as a freeze operation of the endoscope image displayed on the screen of the monitor 6, the switching operation lever 39a which switches the transmitting portion 32 with the clutch to the status for restoring the transmission of the driving force or the status for disconnecting the transmission of the driving force, and a status detecting switch 33 as status detecting means which detects whether the switching operation lever 39a is at the position for instructing the freely bending operation or at the position for instructing the angle operation.

The joystick 36 instructs the bending status of the bending portion 23 by inclining the stick portion 36a and thus changing an inclining angle and an inclining direction thereof. That is, as will be described later, the inclining direction of the joystick 36 corresponds to the bending direction of the bending portion 23 and the inclining angle thereof corresponds to the bending angle of the bending portico 23. For example, when the stick portion 36a of the joystick 36 is in a straight status, the bending portion 23 enters a non-bending status (straight status).

A relative relationship is established between the inclining angle of the stick portion 36a in the joystick 36 and the bending angle of the bending portion 23. That is, the amount of change in inclining angle of the stick portion 36a is proportional to the amount of change in bending angle of the bending portion 23. The bending potion 23 is not necessarily in the non-bending status (straight status) when the stick portion 36a is in the straight status.

Referring to FIG. 2, the joystick 36 comprises the motor 50 for the stick portion as motive means of an instructing member which restores the inclining angle of the stick portion 36a to the corresponding bending angle of the bending portion 23. The motor 50 for the stick portion comprises two JS motors 51 and 52, corresponding to vertical and horizontal directions of the bending portion 23.

The first JS motor 51 drives the stick portion 36a via a first transmitting gear-train 53 so that the inclining angle changes in the vertical direction. The second JS motor 52 drives the stick portion 36a via a second transmitting gear-train 54 so that the inclining angle changes in the horizontal direction. The motors 51 and 52 change the status of the stick portion 36a when the transmitting portion 32 with the clutch is in the status for disconnecting the transmission of the driving force.

Reference numeral 39b denotes a switch for a abnormal timing which forcedly switches the status for restoring the transmission of the driving force of the transmitting portion 32 with the clutch to the status for disconnecting the transmission of the driving force. When the transmitting portion 32 with the clutch is in the status for restoring the transmission of the driving force, the switch 39b for the abnormal timing is operated and the switching operation lever 39a is operated at the position for instructing the freely bending operation. As a result, the bending portion is forcedly switched to the freely bending status.

The bending control device 3 will be described again with reference to FIG. 1.

The bending control device 3 comprises a bending angle calculating portion 44 which calculates information on the bending status including the bending direction and the bending angle of the bending portion 23 based on an output signal which is outputted from the potentiometer 34, the motor driving signal generating portion 42 which compares a calculated value by the bending angle calculating portion 44 with the signal for instructing the bending operation outputted from the joystick 36, generates a driving signal for bending the bending portion 23 so that the absolute position of the bending portion 23 matches that indicated by the signal for instructing the bending operation, and outputs the driving signal to the corresponding bending motor 31, a JS-motor driving signal generating portion 45 as a portion for generating a driving signal of the instructing member that forms positioning means, which calculates the inclining direction and the inclining angle of the stick portion 36a of the joystick 36 as the instructing statuses thereof based on the information on the bending status calculated by the bending angle calculating portion 44 and which generates and outputs driving signals of the JS motors 51 and 52 that move the stick portion 36a to the calculated position, and a calibration instructing portion 43 which receives the position signal from the status detecting switch 33 that detects the position for instructing the operation of the switching operation lever 39a, outputs to the JS motors 51 and 52, the driving signals thereof generated by the JS-motor driving signal generating portion 45, and instructs the calibration operation.

A description is given of the freely bending operation and the angle operation with reference to a flowchart shown in FIG. 3. In the following description, it is assumed that the bending status of the bending portion 23 matches the inclining direction and the inclining angle of the stick portion 36a in an initial status.

When the endoscope is operated by electrically bending the bending portion 23 and the bending portion 23 is in the freely bending status, in step S1, the switching operation lever 39a is switched to the position for instructing the freely bending operation from the position for instructing the angle operation.

Then, in step S2, the clutch mechanism portion 32a in the transmitting portion 32 with the clutch enters the status for disconnecting the transmission of the driving force, thus the bending portion 23 is set to the freely bending status. The status detecting switch 33 outputs to the bending control device 3, a signal indicating the switching operation lever 39a is at the position for instructing the freely bending operation. In this case, the bending status of the bending portion 23 freely changes due to the external force.

In step S3, the signal from the status detecting switch 33 is inputted and the calibration instructing portion 43 in the bending control device 3 outputs an instructing signal of such the calibration operation that the bending status of the bending portion 23 matches the instructing status of the stick portion 36a.

In step S4, the JS-motor driving signal generating portion 45 outputs to the JS motors 51 and 52, a driving signal thereof generated based on the calculated value of the bending angle calculating portion 44 for calculating the change in bending status of the bending portion 23. Then, the stick portion 36a in the joystick 36 is driven by the JS motors 51 and 52. Consequently, in step S5, the bending status of the bending portion 23 matches the inclining direction and the inclining angle of the stick portion 36a.

In the freely bending status, the inclining direction and the inclining angle of the stick portion 36a continuously changes so that they match the change in the bending status of the bending portion 23 under the driving operation of the JS motors 51 and 52.

Namely, in the freely bending status, the relation just before shifting to the freely bending status is maintained between the bending status of the bending portion 23 and the inclining direction and the inclining angle of the stick portion 36a. According to the first embodiment, the calibration is carried out by the shift to the freely bending status in views of the foregoing.

After that, when the bending portion 23 in the freely bending status is electrically bent again, in step S6, the switching operation lever 39a is switched to the position for instructing the angle operation from the position for instructing the freely bending operation.

Then, in step S7, the clutch mechanism portion 32a in the transmitting portion 32 with the clutch is in the status for restoring the transmission of the driving force. On the other hand, the status detecting switch 33 outputs to the bending control device 3, a signal indicating the switching operation lever 39a is at the position for instructing the angle operation.

In step S8, the calibration instructing portion 43 outputs a signal indicating the calibration operation stops and, thus, the output of the driving signal from the JS-motor driving signal generating portion 45 to the JS motors 51 and 52 stops, thereby entering the status for the angle operation.

As a result, the bending status of the bending portion 23 changes in accordance with the signal for instructing the bending operation outputted from the joystick 36 by properly operating the joystick 36. In this case, the bending status of the bending portion 23 matches the inclining direction and the inclining angle of the stick portion 36a and therefore the signal for bending operation is outputted as the absolute-position signal.

The above-mentioned calibration operation is not limited to the case in which the bending portion 23 is in the freely bending status. It may be performed, before the bending operation, by using a straight-pipe shaped tool 61 for setting the non-bending status having a piercing hole 61a with a predetermined diameter as means for setting the non-bending status corresponding to the positioning means for setting the bending portion 23 to the straight status as shown in FIG. 4. As a result of the calibration operation, the bending status of the bending portion 23 matches the inclining direction and the inclining angle of the stick portion 36a.

Referring to FIG. 5, when the calibration operation is executed by using the tool 61 for setting the non-bending status, in step S11, an operator first inserts the bending portion 23 into the piercing hole 61a, thereby setting the bending portion 23 to the non-bending status.

In step S12, the signal outputted from the status detecting switch 33 is checked. When the status detecting switch 33 outputs to the bending control device 3, the signal indicating the switching operation lever 39a is at the position for instructing the freely bending operation, the bending portion 23 is in the non-bending status. Then, the processing routine advances to step S13.

At this time point, the calibration instructing portion 43 does not output the signal for instructing the calibration operation and the stick portion 36a can be set to an arbitrary status by the operator. The operator sets the stick portion 36a to, e.g., the straight status.

In step S13, the calibration instructing portion 43 outputs the signal for instructing the calibration operation. Accordingly, in step S14, the JS-motor driving signal generating portion 45 outputs the driving signal to the JS motors 51 and 52. In step S15, the JS motors 51 and 52 drive the stick portion 36a, the status of the stick portion 36a changes in accordance with the change in the bending portion 23 in the non-bending status, and the calibration operation is implemented. For example, when the bending portion 23 is in the non-bending status, the stick portion 36a is set to the straight status.

After that, the bending portion 23 is in the status for the angle operation by switching the switching operation lever 39a to the position for instructing the angle operation.

In step S12, when the status detecting switch 33 outputs to the bending control device 3, the signal indicating that the switching operation lever 39a is at the position for instructing the angle operation, the tool 61 for setting the non-bending status cannot be arranged to the bending portion 23.

Therefore, the processing routine advances to step S16 whereupon the switching operation lever 39a is switched to the position for instructing the freely bending operation and then the processing routine returns to step S11.

In place of executing the calibration operation while the tool 61 for setting the non-bending status is inserted in the bending portion 23 and it is in the non-bending status, the calibration operation may be implemented by manually setting the bending portion 23 to the non-bending status by the operator. The JS motors 51 and 52 drive the stick portion 36a, thus entering the instructing status corresponding to the bending status of the bending portion 23 and completing the calibration operation.

That is, the operator arranges the switching operation lever 39a to the position for instructing the freely bending operation. Consequently, the JS motors 51 and 52 are driven irrespective of the bending status of the bending portion 23 and the calibration operation is performed so that the instructing status of the stick portion 36a matches the bending status of the bending portion 23.

A description is given of the operation of the electrically bending endoscope apparatus 1 with the above-mentioned structure.

The electric bending endoscope apparatus 1 is configured by connecting the devices 3, 4, 5, 6, and 7 to the electric bending endoscope 2 which is subjected to sterilization process and in which the clutch mechanism portion 32a in the transmitting portion 32 with the clutch is in the status for disconnecting the transmission of the driving force, namely, in the freely bending status. Then, the power of the devices 3, 4, 5, 6, and 7 is turned on.

Then, the status detecting switch 33 outputs to the bending control device 3, the signal indicating that the switching operation lever 39a is at the position for instructing the freely bending operation. Thus, the calibration instructing portion 43 in the bending control device 3 outputs the signal for instructing the calibration operation in which the bending status of the bending portion 23 matches the instructing status of the stick portion 36a. The JS motors 51 and 52 drive the stick portion 36a in the joystick 36 and the bending status of the bending portion 23 thus matches the inclining direction and the inclining angle of the stick portion 36a.

The switching operation lever 39a is switched to the position for instructing the angle operation, thereby enabling the inserting portion 20 to be inserted in the celom while bending the bending portion 23 by the joystick 36. On the other hand, the inserting portion 20 is inserted in the celom in the freely bending status by setting the switching operation lever 39a to the position for instructing the freely bending operation without switching the switching operation lever 39a. Thus, the operator properly selects the bending portion 23 to the freely bending status or the status for the angle operation, and the operation for inserting the inserting portion 20 in the celom is executed.

After the observation, the inserting portion 20 is removed from the luminal portion. The switching operation lever 39a is switched to the position for instructing the freely bending operation, the clutch mechanism portion 32a in the transmitting portion 32 with the clutch is set to the status for disconnecting the transmission of the driving force, and the examination using the endoscope ends.

Upon the calibration operation, the tool 61 for setting the non-bending status is attached to the bending portion 23 and the calibration operation is performed, so that the stick portion 36a is in the straight status.

When an inconvenience such as the overdriving of the bending motor 31 is found during the manual operation, the switch 39*a* for the abnormal timing is operated. Consequently, the bending wire 24 is irreversibly disconnected and is set to the freely bending status. An outer surface of the switch 39*b* for the abnormal timing may be colored red. Alternatively, the switch 39*b* for the abnormal timing may be arranged at a position different from the operating portion 30, e.g., at the bending control device 3.

Further, according to the first embodiment, the means for detecting the bending angle is the potentiometer 34. However, it is not limited to the potentiometer and may use others such as a tension sensor for detecting the tension of the bending wire 24 by using a distortion gauge and dynamic feed-back or the combination of the potentiometer and the tension sensor.

As mentioned above, the switching operation lever is arranged at the position for instructing the freely bending operation, and the clutch mechanism portion in the transmitting portion with the clutch mechanism is set to the status for disconnecting the transmission of the driving force, and the freely bending status in which the tension of the bending wire is released is easily set.

Further, the status detecting switch detects that the switching operation lever is at the position for instructing the freely bending operation and, thus, the calibration instructing portion instructs the calibration operation for outputting the driving signal to the JS motors to the JS-driving signal generating portion so as to perform the calibration operation in which the bending status of the bending portion matches the inclining status of the stick portion in the joystick.

Consequently, even when the inserting portion is inserted in the celom, the calibration operation is performed by returning the freely bending status to the status for the angle operation. When the operator switches the switching operation lever from the position for instructing the freely bending operation to the position for instructing the angle operation, the bending status of the bending portion matches the instructing status of the stick portion. As a result, the operator can operate the endoscope without recognizing the calibration operation. Further, the inserting portion is inserted in the celom in the freely bending status, thus, the stick portion moves in accordance with the changing status of the bending operation of the bending portion, and the bending status in the celom can easily be grasped.

In addition, the tool for setting the non-bending status is attached to the bending portion and the calibration operation is performed, thereby enabling the calibration operation while the stick portion in the joystick is in the straight status.

Accordingly, the operator manually implements the calibration operation of the electric bending endoscope before the operation, and recognizes a unique relationship between the bending status of the bending portion and the operating status of the joystick in the electric bending endoscope.

The above description is given of the calibration operation in which the bending status of the bending portion 23 changes in the freely bending status and the instructing status of the stick portion 36*a* in the joystick 36 always matches the change in bending status of the bending portion 23 by driving the JS motors 51 and 52. However, when the switching operation lever 39*a* is switched to the position for instructing the angle operation from the position for instructing the freely bending operation, the driving signal obtained by calculating the bending status of the bending portion 23 by the bending angle calculating portion 44 may be outputted to the JS motors 51 and 52. Consequently, the switching operation lever 39 is switched to the position for instructing the angle operation, the JS motors 51 and 52 are driven, and the calibration operation may be performed so that the bending status of the bending portion 23 matches the instructing status of the stick portion 36*a*.

The above description is given of the clutch mechanism portion having the mechanical structure according to the first embodiment. However, the clutch mechanism portion is not limited to this and it may be an electric clutch mechanism such as an electromagnetic clutch.

Figure 6:
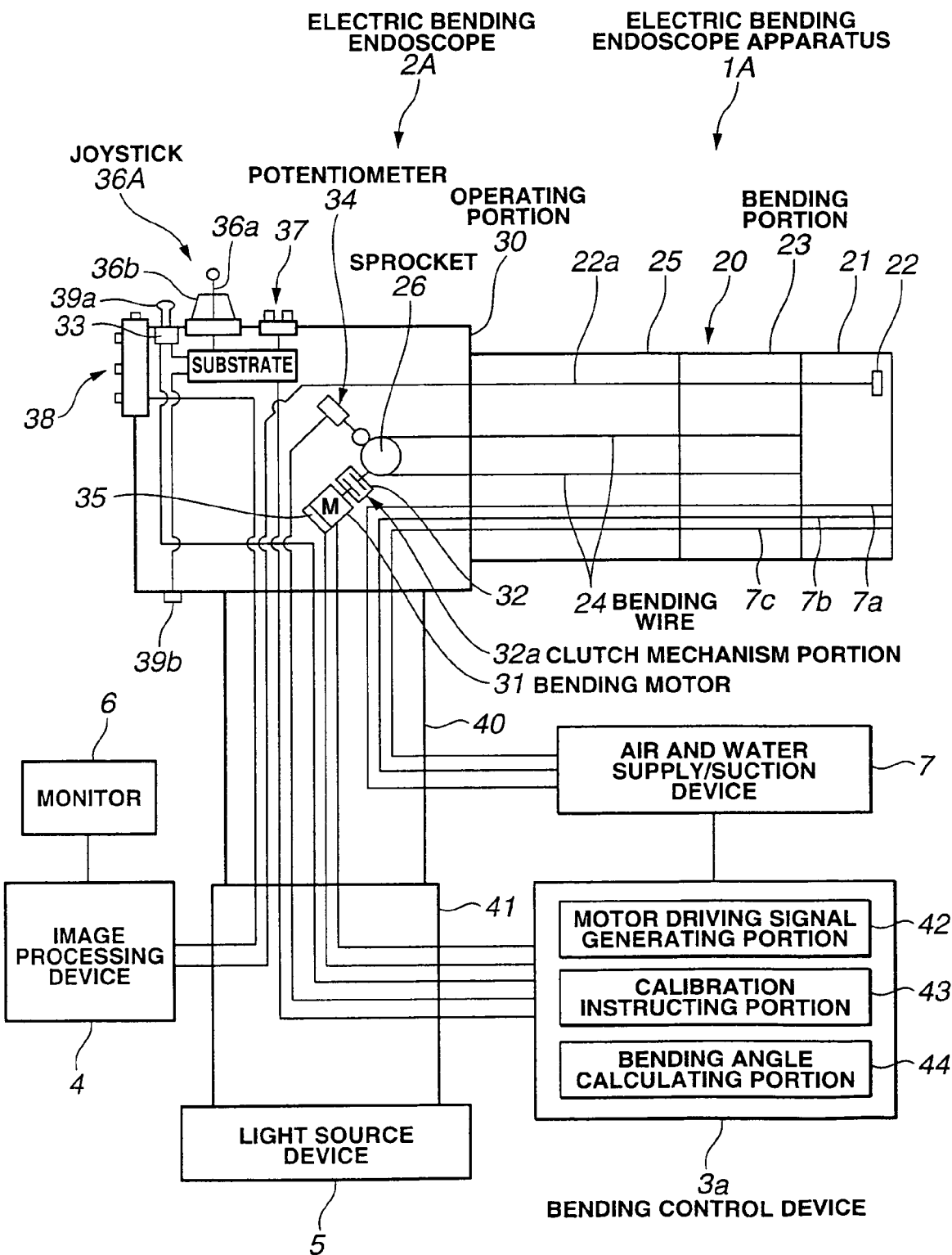
FIG. 6 is a diagram for explaining one construction of an electric bending endoscope apparatus according to a second embodiment.
Figure 7:
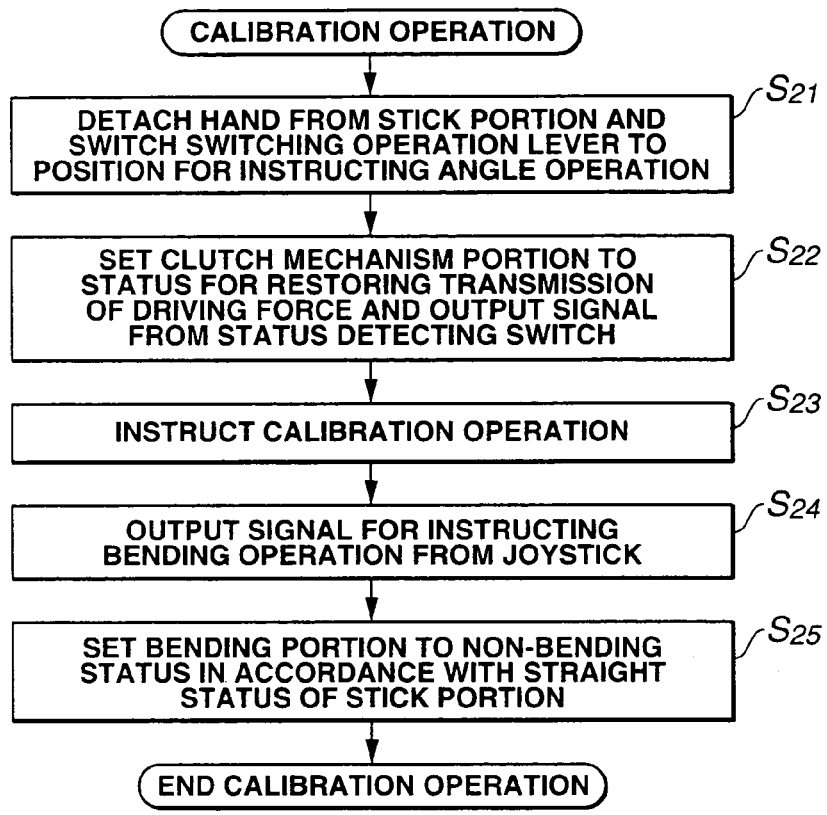
FIG. 7 is a flowchart for explaining a calibration operation.

A second embodiment of the present invention will be described with reference to FIGS. 6 and 7. FIG. 6 is a diagram for explaining the structure of an electric bending endoscope apparatus. FIG. 7 is a flowchart for explaining the calibration operation.

The motor 50 for the stick portion is provided for the joystick 36 for the calibration operation in which the motor 50 for the stick portion changes the instructing status of the stick portion 36*a* to match the bending status of the bending portion 23 according to the first embodiment. However, referring to FIG. 6, an energizing member 36*b* as positioning means is arranged around a stick portion 36*a* in a joystick 36A so that the stick portion 36*a* is independently straight, in place of arranging the motor 50 for the stick portion to the joystick 36A in an electric bending endoscope 2A in an electric bending endoscope apparatus 1A according to the second embodiment.

Further, according to the second embodiment, a bending control device 3A does not use the JS-motor driving signal generating portion 45 which generates the driving signal for driving the motor 50 for stick portion. Other structures are the same as those according to the first embodiment, the same reference numerals denote the same components, and they are not described.

A description is given of the calibration operation of the electric bending endoscope 2A with the above-mentioned structure.

According to the second embodiment, the calibration operation is implemented by using characteristics of the joystick 36A. That is, referring to FIG. 7, in step S21, upon the calibration operation, the operator switches the switching operation lever 39*a* to the position for instructing the angle operation without touching the stick portion 36*a* in the joystick 36A.

In step S22, the clutch mechanism portion 32*a* in the transmitting portion 32 with the clutch is set to the status for restoring the transmission of the driving force and the status detecting switch 33 outputs to the bending control device 3, a signal indicating that the switching operation lever 39*a* is at the position for instructing the angle operation.

In step S23, the calibration instructing portion 43 outputs a signal instructing the calibration operation in which the bending status of the bending portion 23 matches the instructing status of the stick portion 36*a*. Thus, in step S24, the joystick 36A in which the stick portion 36*a* is straight outputs the signal for instructing the bending operation. In step S25, the calibration operation is performed so that the bending portion 23 is in the non-bending status (straight status) and it ends.

As mentioned above, the calibration operation is executed so that the bending portion is in the non-bending status (straight status) in accordance with the straight status of the stick portion by switching the switching operation lever to the position for instructing the angle operation while the operator detouches his hand from the stick portion.

Consequently, the operator manually implements the calibration operation of the electric bending endoscope before the operation, and can operate, recognizing a unique relationship between the bending status of the bending portion and the operating status of the joystick in the electric bending endoscope.

Figure 8:
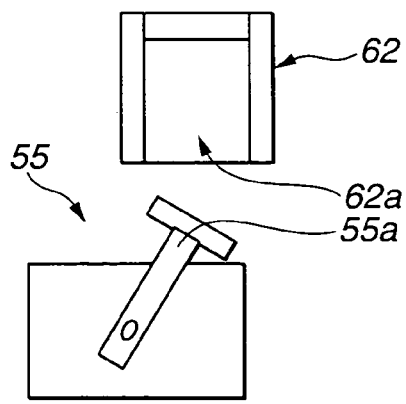
FIG. 8 is a diagram showing a modification of the second embodiment.

FIG. 8 is a diagram showing a modification of the second embodiment.

Referring to FIG. 8, according to the modification of the second embodiment, when the energizing member is not arranged around the stick portion 55a, the stick portion 55a does not return to the straight status as a neutral position. Therefore, a tool 62 for setting the straight position is provided for the operating switch 55 with the above-mentioned structure of the joystick as means for setting the neutral position corresponding to the positioning means which arranges the stick portion 55a to the straight neutral position.

A hollow portion 62a is provided to the tool 62 for setting the straight position. The stick portion 55a is arranged in the hollow portion 62a, an end surface on the opening of the hollow portion 62a comes into contact with an upper surface of the operating switch 55, and the stick portion 55a is thus arranged to the neutral position at which the stick portion 55a is straight.

In this status, the operator switches the switching operation lever 39a to the position for instructing the angle operation, thereby executing the calibration operation in which the bending portion 23 is set to the non-bending status in accordance with the straight status of the stick portion 55a. Accordingly, the same operations and advantages are obtained.

Figure 9:
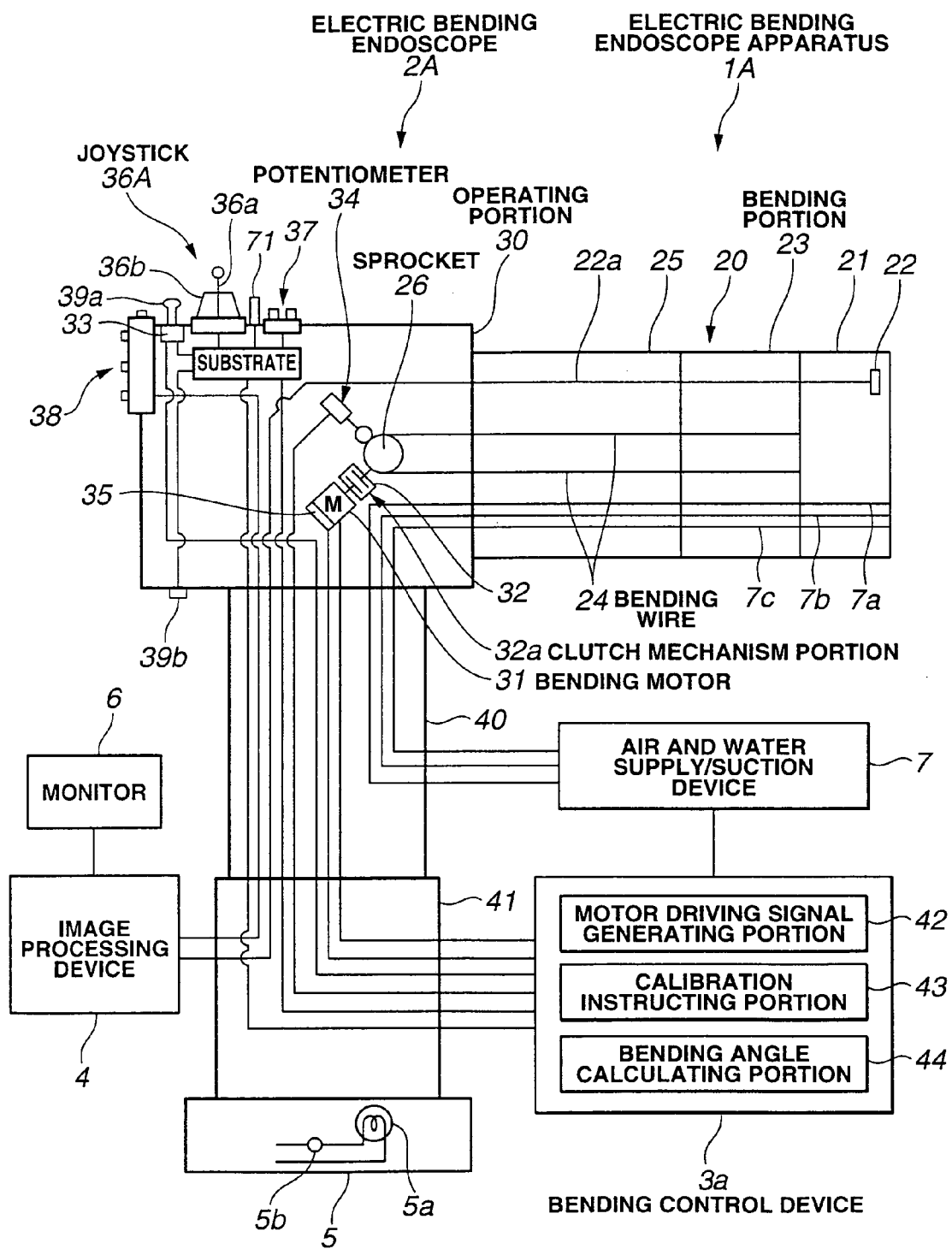
FIG. 9 is a diagram showing another construction of the electric bending endoscope apparatus.

Referring to FIG. 9, another structure of the electric bending endoscope apparatus is shown and a calibration switch 71 directly connected to the calibration instructing portion 43 is arranged to the operating portion 30 and the calibration switch 71 may be operated, thereby performing the calibration operation. With the structure, the switching operation lever 39a corresponds to a lever for switching the clutch mechanism.

Figure 10:
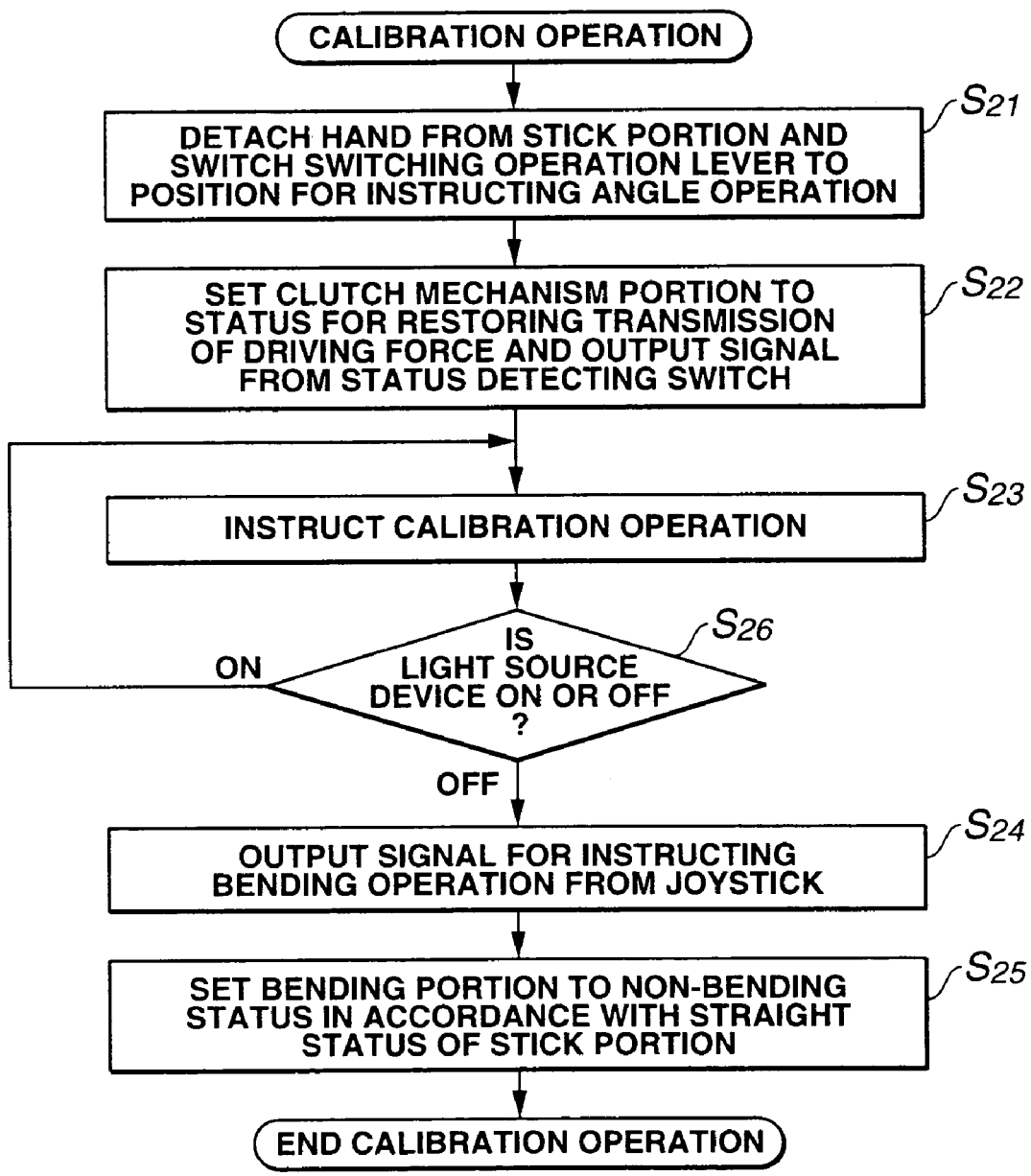
FIG. 10 is a flowchart for explaining a calibration operation.

The bending portion 23 is in the straight status in the calibration operation. Therefore, referring to FIG. 10 showing a flowchart for explaining the calibration operation, step S26 whereupon it is checked whether the light source device 5 is ON or OFF is set between steps S23 and S24 so that the start of the calibration operation is prevented when the calibration switch is erroneously operated upon inserting the inserting portion 20 in the celom.

In other words, the light source device 5 includes a lamp status detecting switch 5b is arranged as a position instruction invalidating portion providing a means for invalidating the restoring instruction which detects whether a lamp 5a, acting as an invalidating instructing portion, is ON or OFF. When it is checked in step S26 that the lamp 5a in the light source device 5 is ON, the instruction for starting the calibration operation by using the calibration switch 71 is canceled and the processing routine returns to step S23. Then, when it is checked in step S26 that the lamp in the light source device 5 is OFF, the processing routine shifts to step S24.

Therefore, when the calibration switch 71 is operated before the operation, the light source device 5 is OFF and the calibration operation is performed.

The calibration operation may be executed by using the tool 62 for setting the straight position and the tool 61 for setting the non-bending status. Or, it may be performed by setting the bending portion 23 to the non-bending status and by using the tool 61 for setting the non-bending status and by manually positioning the stick portion 55a to the straight status. Alternatively, it may be implemented by setting the stick portion 55a by using the tool 62 for setting the straight position and by manually setting the bending portion 23 to the non-bending status. Or, it may be performed by visually setting the bending portion 23 to the non-bending status and by visually setting the stick portion 55a to the straight status.

FIGS. 11A and 11B are diagrams for explaining the structure of the clutch mechanism portion for the calibration operation.

Referring to FIGS. 11A and 11B, since the clutch mechanism portion 66 is the positioning means according to the second embodiment, the engagement of the clutch mechanism portion 66 is unique. That is, referring to FIG. 11B, a gear portion 64 in the clutch mechanism portion 66 includes a projected portion 64a and a hollow portion 64b which are lozenge-shaped. The amount of revolution of a first clutch 66a is set to 180°. The first clutch 66a is driven by a gear train 65 as the means for transmitting the driving force which transmits the driving force of the bending motor 31. Therefore, a second clutch 66b stretches the bending wire 24 by the rotating at an angle of 180° as shown by an arrow.

The second clutch 66b shown in FIG. 11B is at the neutral position. In this status, the bending portion 23 is set to the non-bending status by engaging the projected portion 64a in the first clutch 66a to the hollow portion 64b in the second clutch 66b.

According to the second embodiment, the status for restoring the transmission of the driving force is set by engaging the first clutch 66a to the second clutch 66b and the bending portion 23 is in the non-bending status. Other operations and advantages are the same as those according to the first embodiment.

Figure 12:
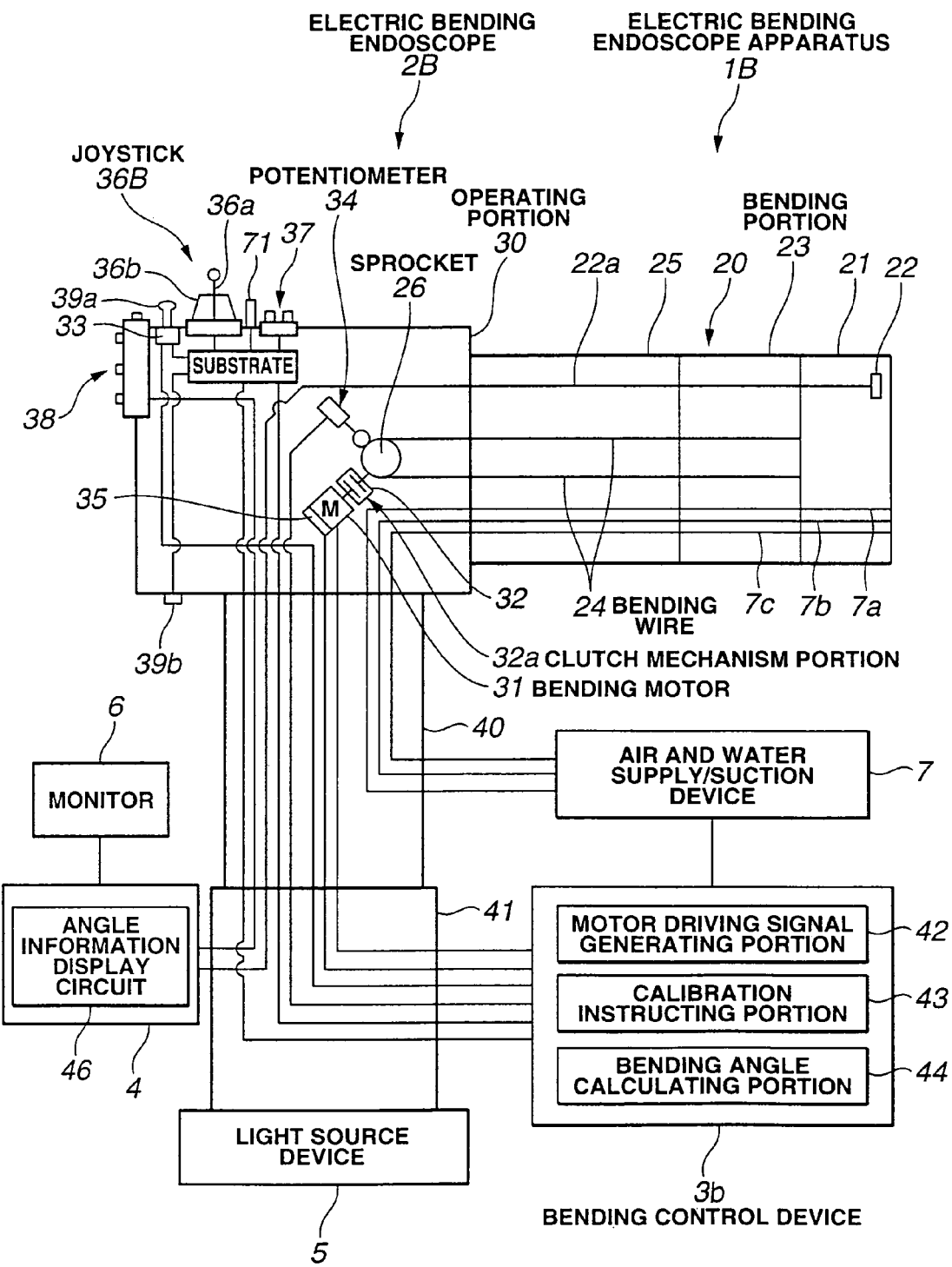
FIG. 12 is a diagram for explaining the construction of an electric bending endoscope apparatus according to a third embodiment.
Figure 13:
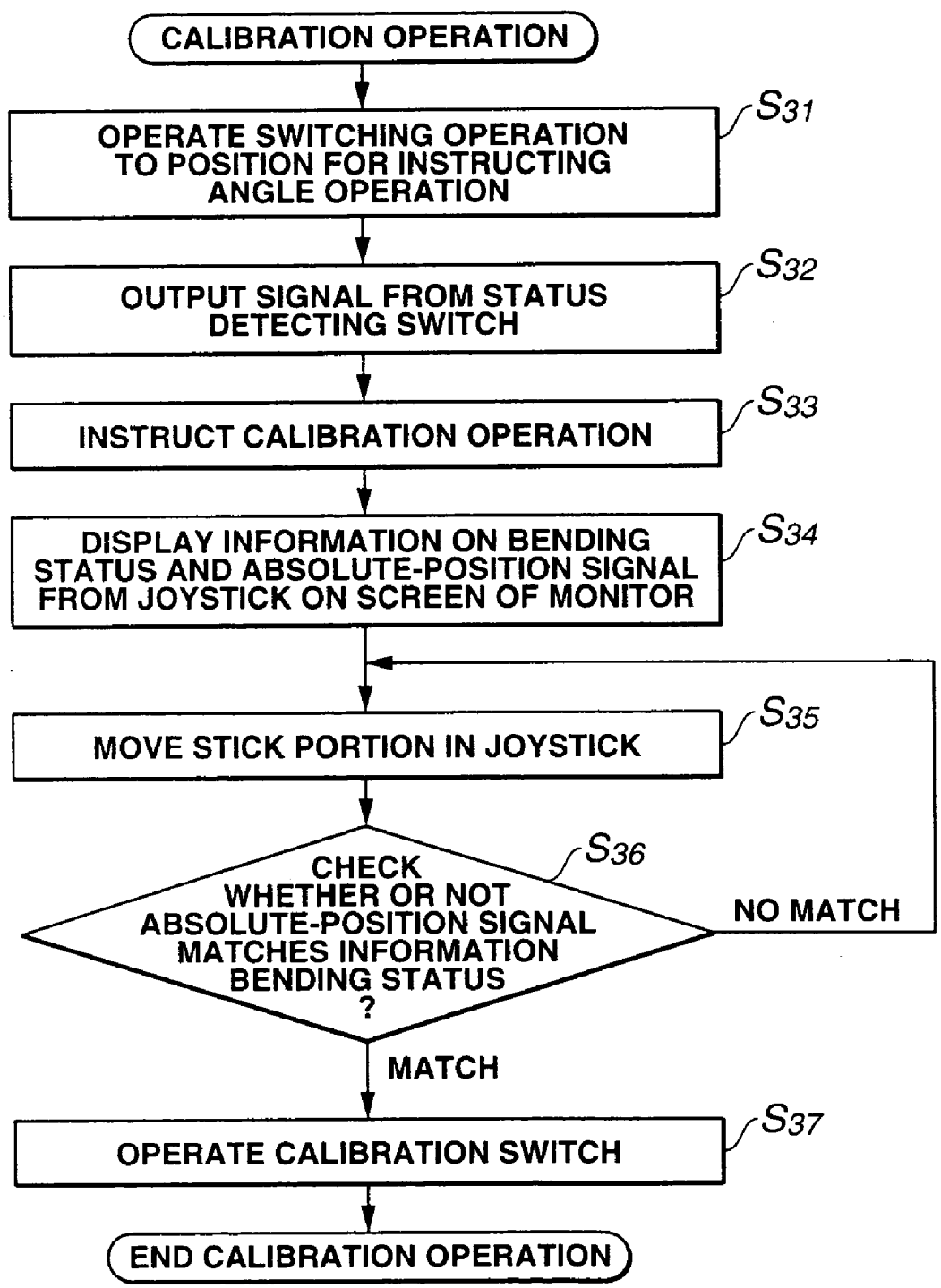
FIG. 13 is a flowchart for explaining a calibration operation.

A description is given of a third embodiment of the present invention with reference to FIGS. 12 to 14. FIG. 12 is a diagram for explaining the structure of an electric bending endoscope apparatus. FIG. 13 is a flowchart for explaining the calibration operation. FIG. 14 is a diagram for explaining an image which is superimposed and displayed on a screen of the monitor.

Referring to FIG. 12, an energizing member 36b is arranged around a stick portion 36a in a joystick 36B so that it is independently straight in an electric bending endoscope 2B in an electric bending endoscope apparatus 1B, in place of arranging the motor 50 for the stick portion, similarly to the electric bending endoscope 2A. According to the third embodiment, the bending control device 3B does not use the JS-motor driving signal generating portion 45 which generates the driving signal for driving the motor 50 for the stick portion.

The image processing device 4 comprises an angle information display circuit 46 as means for displaying angle information corresponding the positioning means which superimposes and displays on the screen of the monitor 6, the information on the bending status indicating the bending status calculated by the bending angle calculating portion 44 and the absolute-position signal outputted from the joystick 36. Other structures are the same as those according to the first and second embodiments, the same reference numerals denote the same components, and they are not described.

A description is given of the calibration operation of the electric bending endoscope 2A with the above structure.

Referring to FIG. 13, in step S31, the switching operation lever 39a is operated at the position for instructing the angle operation in the freely bending status in which the bending status of the bending portion 23 freely changes under the influence of the external force. In step S32, the status detecting switch 33 outputs a signal to the bending control device 3. In step S33, the calibration instructing portion 43 outputs to the angle information display circuit 46, a signal indicating that the information on the bending status and the absolute-position signal are displayed on the screen. In step S34, the information on the bending status 68 and the absolute-position signal 69 are superimposed and displayed on the endoscope image displayed on a screen 6a shown in FIG. 14.

In step S35, the operator operates the stick portion 36a in the joystick 36A to execute the calibration operation in which the absolute-position signal outputted as the instructing status matches the information on the bending status of the bending portion 23. In this case, since the stick portion 36a moves, the absolute-position signal 69 displayed on the screen 6a sequentially changes.

In step S36, it is checked whether or not the absolute-position signal 69 matches the information on the bending status 68. If YES in step S36, the end of the calibration operation is notified to the operator by information and illumination as notifying means. Further, the calibration instructing portion 43 determines the end of the calibration, the superimposing and display operation is canceled on the screen, and the calibration operation ends. Thus, the status for the angle operation is set to change the bending status of the bending portion 23 by inclining the joystick 36B.

The information on the bending status may always be displayed on a part of the screen 6a.

As mentioned above, the information on the bending status of the bending portion is displayed on the screen and the calibration operation is performed by moving only the stick portion so that it matches the information on the bending status. Accordingly, similarly to the first embodiment, the calibration operation can easily be executed when returning to the status for the angle operation after the freely bending operation in the status in which the inserting portion is inserted in the celom.

The observing status can easily be grasped by displaying the information on the bending status of the bending portion on the screen. Other operations and advantages are the same as those according to the first and second embodiments.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electric bending endoscope, comprising:
    an inserting portion that is inserted into a subject, the inserting portion having a bending portion that can be bent in accordance with an operation;
    a bending instructing member which provides a bending instruction for bending the bending portion in a desired status, the bending instructing member being operated by an operator and outputting a bending instruction signal for matching the bending status of the bending portion to a bending status based on a value instructed by the bending instructing member when the bending portion is instructed so as to be bent by the bending instructing member;
    a bending motive device for supplying power to bend the bending portion based on the bending instruction signal;
    a detecting device for detecting the bending status of the bending portion;
    a bending angle calculating portion for calculating a value indicative of the bending status of the bending portion based on the bending status of the bending portion detected by the detecting device;
    a driving force transmission switching portion connected to the bending motive device and the bending portion, the driving force transmission switching portion being able to selectively switch between the status in which the bending motive device and the bending portion are connected so that the power supplied by the bending motive device may be transmitted to the bending portion and the status in which the bending motive device and the bending portion are disconnected so that the power supplied by the bending motive device may not be transmitted to the bending portion, the bending portion being able to be bent in the status in which the value instructed by the bending instructing member and the value calculated by the bending angle calculating portion do not coincide with each other in the status in which the bending motive device and the bending portion are disconnected by the driving force transmission switching portion;
    a judging portion for judging whether the instructed value and the calculated value coincide with each other;
    a positioning control portion for validating or invalidating the bending instruction signal in response to the switching between the connected status and the disconnected status by the driving force transmission switching portion, the bending motive device being operative based on the bending instruction signal in the status in which the bending instruction signal is validated by the positioning control portion, the bending motive device being not operative based on the bending instruction signal in the status in which the bending instruction signal is invalidated, the positioning control portion invalidating the bending instruction signal when the bending motive device and the bending portion are switched from the connected status to the disconnected status and validating the bending instruction signal when the bending motive device and the bending portion are switched from the disconnected status to the connected status if the judging portion judges that the instructed value and the calculated value coincide with each other.

2. An electric bending endoscope according to claim 1, further comprising: a positioning instructing portion for providing the bending motive device with a positioning instruction to bend the bending portion so that the instructed value and the calculated value may coincide with each other when the bending motive device and the bending portion are switched from the disconnected status to the connected status by the driving force transmission switching portion, the positioning instructing portion finishing the positioning instruction if the judging portion judges that the instructed value and the calculated value coincides with each other in response to the bending based on the positioning instruction and the positioning control portion validating the bending instruction signal.

3. An electric bending endoscope according to claim 1, further comprising:
    a driving member for driving the bending instructing member; and
    a positioning instructing portion for providing the driving member for driving the bending instructing member with an instruction to drive the bending instructing member so that the instructed value and the calculated value may coincide with each other when the bending motive device and the bending portion are switched from the disconnected status to the connected status by the driving force transmission switching portion, the positioning instructing portion finishing the instruction to drive the bending instructing member if the judging portion judges that the instructed value and the calculated value coincide with each other in response to the driving of the bending instructing member based on the instruction to drive the bending instructing member and the positioning control portion validating the bending instruction signal.

4. An electric bending endoscope apparatus according to claim 3, further comprising:

a tool for setting the non-bending status which sets the bending portion to be in a straight status, wherein the positioning instructing portion provides the driving member for driving the bending instructing member with an instruction for driving the bending instruction member so that the calculated value based on the bending status set by the tool for setting the non-bending status and the instructed value may coincide with each other.

5. An electric bending endoscope according to claim 4, wherein the tool for setting the non-bending status is a tubular member that is mounted on the outer periphery of the bending portion.

6. An electric bending endoscope according to claim 1, further comprising: a switching instructing portion for providing an instruction to operate the driving force transmission switching portion in order to switch between the connected status and the disconnected status of the bending motive device and the bending portion.

7. An electric bending endoscope according to claim 1, further comprising: a status displaying portion for displaying the value instructed by the bending instructing member and the value calculated by the bending angle calculating portion.

8. An electric bending endoscope according to claim 1, further comprising:

an image pickup device provided in the inserting portion;
a display portion for displaying an image obtained by the image pickup device; and a status displaying control portion for displaying the value instructed by the bending instructing member and the value calculated by the bending angle calculating portion.

9. An electric bending endoscope according to claim 8, wherein the status displaying control portion displays the value instructed by the bending instructing member and the value calculated by the bending angle calculating portion on the display portion when the bending motive device and the bending portion are switched from the connected status to the disconnected status by the driving force transmission switching portion.

10. An electric bending endoscope according to claim 1, further comprising: a notifying portion for notifying the operator of the instructed value and the calculated value when the bending motive device and the bending portion are switched from the connected status to the disconnected status by the driving force transmission switching portion.

11. An electric bending endoscope according to claim 1, further comprising: a notifying portion for notifying the operator of the result of judgment when the judging portion has judged that the instructed value does not coincide with the calculated value in the status in which the bending motive device and the bending portion are switched from the disconnected status to the connected status by the driving force transmission switching portion.

12. An electric bending endoscope according to claim 1, further comprising: a notifying portion for notifying the operator of the result of judgment when the judging portion has judged that the instructed value coincides with the calculated value in the status in which the bending motive device and the bending portion are switched from the disconnected status to the connected status by the driving force transmission switching portion.

13. An electric bending endoscope according to claim 1, wherein the bending instructing member further comprises a lever member which can be moved in a plurality of directions, the bending instructing member outputting the bending instruction signal in response to the movement of the lever member.

14. An electric bending endoscope according to claim 13, wherein the bending instructing member further comprises a fixing member for fixing the lever member at a set position.

15. An electric bending endoscope according to claim 13, further comprising a neutral position setting member for moving the lever member to a neutral position, the bending instructing member outputting an instruction signal for making straight the bending portion in the status in which the lever member is positioned in the neutral position.

16. An electric bending endoscope according to claim 1, wherein the bending motive device has a motor, and the driving force transmission switching portion has an operation wire connected to the bending portion to bend the bending portion, a sprocket for pulling the operation wire based on the power supplied from the motor and a clutch capable of selectively switching between the connecting status to transmit the power by the motor to the sprocket and the disconnecting status not to transmit the power by the motor to the sprocket.

* * * * *